United States Patent [19]

Hunter et al.

[11] 4,201,724
[45] May 6, 1980

[54] N³-(CYCLOALKYL)ALKYL-2,4-DINITRO-6-TRIFLUOROMETHYL-1,3-PHENYLENEDIAMINE COMPOUNDS

[75] Inventors: Don L. Hunter, Anaheim; William G. Woods, Fullerton, both of Calif.

[73] Assignee: United States Borax & Chemical Corp., Los Angeles, Calif.

[21] Appl. No.: 716,487

[22] Filed: Aug. 20, 1976

Related U.S. Application Data

[63] Continuation of Ser. No. 551,480, Feb. 20, 1975, abandoned, which is a continuation-in-part of Ser. No. 383,004, Jul. 26, 1973, abandoned.

[51] Int. Cl.² .............................................. C07C 87/62
[52] U.S. Cl. ...................................... 260/577; 71/121; 260/573
[58] Field of Search ........................... 260/577; 71/121

[56] References Cited

U.S. PATENT DOCUMENTS

| 3,546,295 | 12/1970 | Maravetz | 260/577 |
| 3,617,252 | 11/1971 | Hunter et al. | 71/121 |

FOREIGN PATENT DOCUMENTS 2447085  4/1975  Fed. Rep. of Germany ........... 260/577

Primary Examiner—John Doll
Attorney, Agent, or Firm—J. R. Thornton

[57] ABSTRACT

N³-(Cycloalkyl)alkyl-2,4-dinitro-6-trifluoromethyl-1,3-phenylenediamine compounds of the formula

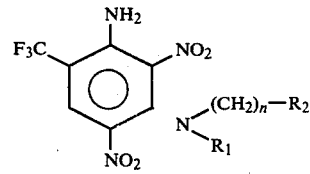

wherein $R_1$ is selected from the group consisting of H—, $C_1$–$C_6$ straight and branched chain alkyl, haloalkyl and hydroxyalkyl, $C_2$–$C_6$ straight and branched chain alkenyl, alkynyl and alkoxyalkyl and $C_3$–$C_6$ cycloalkyl; $R_2$ is selected from the group consisting of $C_3$–$C_5$ cycloalkyl groups and $C_3$–$C_5$ cycloalkyl groups substituted with $C_1$–$C_6$ straight and branched chain alkyl; and n is 1, 2 or 3. The compounds are useful in herbicidal compositions.

3 Claims, No Drawings

$N^3$-(CYCLOALKYL)ALKYL-2,4-DINITRO-6-TRI-FLUOROMETHYL-1,3-PHENYLENEDIAMINE COMPOUNDS

This is a continuation of application Ser. No. 551,480 filed Feb. 20, 1975, now abandoned, which in turn is a continuation-in-part of our application Ser. No. 383,004, filed July 26, 1973, now abandoned.

SUMMARY OF THE INVENTION

This invention relates to novel $N^3$-(cycloalkyl)alkyl-2,4-dinitro-6-trifluoromethyl-1,3-phenylenediamine compounds which have outstanding herbicidal activity.

The novel compounds of this invention can be defined by the formula

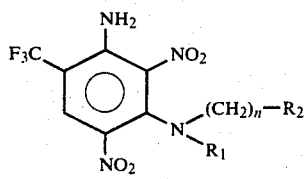

wherein $R_1$ is selected from the group consisting of H—, $C_1$–$C_6$ straight and branched chain alkyl, haloalkyl and hydroxyalkyl, $C_2$–$C_6$ straight and branched chain alkenyl, alkynyl, and alkoxyalkyl and $C_3$–$C_6$ cycloalkyl; $R_2$ represents a substituent selected from the group consisting of $C_3$–$C_5$ cycloalkyl groups and $C_3$–$C_5$ cycloalkyl groups substituted with $C_1$–$C_6$ straight and branched chain alkyl; and n is selected from the group consisting of 1, 2, and 3.

Typical examples of the groups represented by $R_1$ are hydrogen, alkyl, alkenyl, and alkynyl groups having up to about 6 carbon atoms, including the cyclic analogues thereof as well as the halo, hydroxy, and lower alkoxy substituted derivatives thereof. Representative groups are methyl, ethyl, n-propyl, isopropyl, n-butyl, sec-butyl, n-pentyl, sec-pentyl, n-hexyl, allyl, 4-methylpentyl, 2-butenyl, 2-butynyl, 3-butynyl, methallyl, 2-pentynyl, 2-hydroxyethyl, 2-bromoethyl, 2-methoxyethyl, 3-ethoxypropyl, 2,2-dimethoxyethyl, 2-chloroallyl, 3-chloropropyl, 4-hydroxybutyl, 2-butynyl, 1-methyl-2-methoxyethyl, 2-bromoallyl, 2-fluoroethyl, propynyl, 4-chloro-2-butenyl, 4-bromo-1-butenyl, 3-iodo-1-pentenyl, 4-chloro-2-butynyl, cyclohexyl, cyclopropyl, cyclobutyl and the like.

A preferred class of compounds according to this invention is that in which $R_1$ represents H— and unsubstituted straight and branched chain alkyl groups containing up to about 6 carbon atoms.

Typical examples of the groups represented by $R_2$ are the $C_3$–$C_5$ cycloalkyl groups, e.g., cyclopropyl, cyclobutyl and cyclopentyl. Optionally, substituted cycloalkyl groups, e.g., methylcyclopropyl and ethylcyclobutyl, are suitable as $R_2$ groups.

A preferred class of compounds according to this invention is that in which $R_2$ represents a $C_3$–$C_4$ cycloalkyl or substituted cycloakyl group.

The value represented by n is an integer of from 1 to 3. A preferred class of compounds is that in which n is 1 and 2.

Representative examples of compounds of the invention are:

$N^3$-Cyclopropylmethyl-$N^3$-methyl-2,4-dinitro-6-trifluoromethyl-1,3-phenylenediamine $N^3$-Cyclopropylmethyl-2,4-dinitro-6-trifluoromethyl-1,3-phenylenediamine $N^3$-Cyclopropylmethyl-$N^3$-ethyl-2,4-dinitro-6-trifluoromethyl-1,3-phenylenediamine $N^3$-Cyclopropylmethyl-$N^3$-n-propyl-2,4-dinitro-6-trifluoromethyl-1,3-phenylenediamine $N^3$-Allyl-$N^3$-cyclopropylmethyl-2,4-dinitro-6-trifluoromethyl-1,3-phenylenediamine $N^3$-Cyclopropylmethyl-$N^3$-methallyl-2,4-dinitro-6-trifluoromethyl-1,3-phenylenediamine $N^3$-(2-Cyclopropylethyl)-$N^3$-methyl-2,4-dinitro-6-trifluoromethyl-1,3-phenylenediamine $N^3$-(2-Cyclopropylethyl)-$N^3$-ethyl-2,4-dinitro-6-trifluoromethyl-1,3-phenylenediamine $N^3$-Cyclopropylmethyl-$N^3$-isopropyl-2,4-dinitro-6-trifluoromethyl-1,3-phenylenediamine $N^3$-n-Butyl-$N^3$-cyclopropylmethyl-2,4-dinitro-6-trifluoromethyl-1,3-phenylenediamine $N^3$-Cyclobutylmethyl-$N^3$-methyl-2,4-dinitro-6-trifluoromethyl-1,3-phenylenediamine $N^3$-Allyl-$N^3$-(2-cyclobutylethyl)-2,4-dinitro-6-trifluoromethyl-1,3-phenylenediamine $N^3$-Cyclopropylmethyl-$N^3$-n-hexyl-2,4-dinitro-6-trifluoromethyl-1,3-phenylenediamine $N^3$-(3-Methylcyclobutyl)methyl-$N^3$-n-propyl-2,4-dinitro-6-trifluoromethyl-1,3-phenylenediamine $N^3$-(Methylcyclopropyl)methyl-2,4-dinitro-6-trifluoromethyl-1,3-phenylenediamine The presently preferred compounds are those of the formula

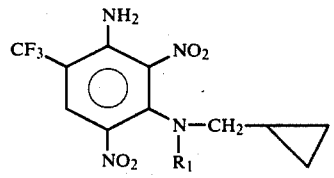

in which $R^1$ is alkyl of 1 to 4 carbon atoms, such as methyl, ethyl, propyl and butyl. Preferably, propyl and butyl are straight chain.

The compounds of this invention are either crystalline solids or high boiling liquids which are generally only slightly soluble in water and moderately soluble in the usual organic solvents such as ethanol, acetone, ether and benzene. They are readily prepared in a two-step reaction starting with a 2,4-dihalo-3,5-dinitrobenzotrifluoride according to the following equation:

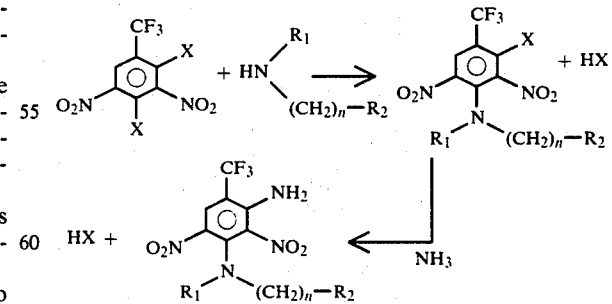

in which X represents a reactive halogen such as chlorine or bromine, and $R_1$, $R_2$ and n have the significance previously assigned.

In the first step of the synthesis, about two moles of the amine $R_1$—$NH(CH_2)_n$—$R_2$ may be used per mole of 2,4-dihalo-3,5-dinitrobenzotrifluoride. If the amine $R_1$—NH(CH$_2$)$_n$—$R_2$ is rare or expensive, it may be convenient to use about one mole of $R_1$—NH—(CH$_2$)$_n$—$R_2$ and about one mole of an HX acceptor, e.g., triethylamine, pyridine, or an inorganic salt such as sodium hydroxide or sodium carbonate, per mole of 2,4-dihalo-3,5-dinitrobenzotrifluoride.

The first halogen atom replaced is that between the two nitro groups on the aromatic ring. This step is advantageously carried out in a non-polar solvent such as a hydrocarbon in which the amine hydrohalide is insoluble and can be removed by filtration. In the second step of the reaction, about two moles or more of ammonia is reacted with intermediate $N^3$-(cycloalkyl)alkyl-2,6-dinitro-3-halo-4-trifluoromethylaniline to form the $N^3$-(cycloalkyl)alkyl-2,4-dinitro-6-trifluoromethyl-1,3-phenylenediamines of this invention.

The second step of the synthesis can be carried out in a sealed reaction vessel, such as a sealed tube or autoclave, to avoid losses of material and to provide easy control of the reaction. When the reagents for the first step of the synthesis have high boiling points, it is unnecessary to use a sealed vessel for the reaction, which may be carried out in the presence of a suitable solvent.

A reaction temperature in the range of from about 20° to about 100° C. preferably is employed to give good yields of the desired product and a satisfactory rate of reaction, both in the case of using a sealed reaction vessel and when the reactants are brought together in the presence of a solvent. Hydrogen halide is formed as a by-product and, in the presence of excess amine, is converted to the amine hydrohalide which can be readily removed by washing with water or by filtration after dissolution of the product mixture in a suitable solvent. The desired products can be purified by well-known procedures such as by recrystallization.

The 2,4-dihalo-3,5-dinitrobenzotrifluoride starting materials are readily prepared by nitration of a 2,4-dihalobenzotrifluoride with a mixture of fuming nitric and fuming sulfuric acids at a temperature below about 80° C.

Amines required for the preparation of the compounds of this invention may be obtained by the methods set forth in U.S. Pat. No. 3,672,864 to Maravetz.

The following examples describe preparation of representative compounds of this invention and intermediates therefor, but it is to be understood that the invention is not to be limited to the specific examples given.

EXAMPLE I

N-Cyclopropylmethyl-N-ethyl-3-chloro-2,6-dinitro-4-trifluoromethylaniline

To a stirred solution of 15.0 grams (0.05 mole) of 2,4-dichloro-3,5-dinitrobenzotrifluoride and 4.97 grams (0.05 mole) of triethylamine in 200 ml. of dimethoxyethane was added, dropwise, 4.28 grams (0.05 mole) of N-cyclopropylmethyl-N-ethylamine at room temperature over a period of 2.5 hours. The resultant mixture was then heated under reflux for 16 hours. The solvent was removed by evaporation under reduced pressure and the residue then dissolved in a mixture of chloroform and water. The organic layer was separated and was washed with water, dilute hydrochloric acid, dilute sodium bicarbonate, and then water. After drying over anhydrous sodium sulfate, the organic solution was evaporated to dryness. The residue was dissolved in hexane and filtered and then evaporated to dryness to give 12.85 grams of the product as as dark, viscous amber liquid.

EXAMPLE II $N^3$-Cyclopropylmethyl-$N^3$-ethyl-2,4-dinitro-6-trifluoromethyl-1,3-phenylenediamine To a glass reactor tube was charged 5.0 grams (0.0135 mole) of N-cyclopropylmethyl-N-ethyl-3-chloro-2,6-dinitro-4-trifluoromethylaniline, 6.8 grams (0.014 mole) of ammonia (as a 7.1% ethanolic solution) and 35 ml. of dimethoxyethane. The tube was sealed and heated in an oven at 105° C. for 40 hours. The reaction tube was cooled and opened. The contents were filtered and the filtrate evaporated to dryness. The residue ws extracted with hot cyclohexane and filtered at room temperature. The filtrate was evaporated under reduced pressure and the residue dissolved in refluxing 95% ethanol. The product crystallized upon cooling and was isolated by filtration to give 2.64 grams of orange crystals, which melted at 99°–100.5° C.

EXAMPLE III $N^3$-Cyclopropylmethyl-$N^3$-n-propyl-2,4-dinitro-6-trifluoromethyl-1,3-phenylenediamine $N^3$-Cyclopropylmethyl-$N^3$-n-propyl-2,4-dinitro-6-trifluoromethyl-1,3-phenylenediamine was obtained by reacting N-cyclopropylmethyl-N-n-propyl-3-chloro-2,6-dinitro-4-trifluoromethylaniline with ammonia according to the procedure of Example II. The product was obtained as yellow-orange crystals melting at 101°–102.5° C.

EXAMPLE IV 2,4-Dichloro-3,5-dinitrobenzotrifluoride

Fuming sulfuric acid (600 ml.) containing 30–33 percent free $SO_3$ was stirred in a two-liter, three-necked flask immersed in an ice bath. Fuming 90 percent nitric acid (585 ml.) was added followed by 148.8 grams (0.692 mole) of 2,4-dichlorobenzotrifluoride. This stirred slurry then was heated to 76° C. and held at 76°±1° C. for 96 hours. The mixture was cooled and the acid was drained from the crust of crystalline product. Water (1,000 ml.) was added to the broken up solid and the stirred slurry extracted with 500 ml. of toluene. The toluene solution, with another 500 ml. of toluene added, was washed successively with water (500 ml.), twice with 500 ml. of 5 percent sodium bicarbonate solution, and finally with water (500 ml.). Removal of the toluene by evaporation at reduced pressure and drying overnight gave 166.6 grams (79%) of the desired 2,4-dichloro-3,5-dinitrobenzotrifluoride, m.p. 67°–72° C. After recrystallization from ethanol the material melts at 74°–75° C.

Reference is made to a patent of Don L. Hunter, U.S. Pat. No. 3,586,725 filed June 12, 1969, which describes and claims preparation of the 2,4-dihalo-3,5-dinitrobenzotrifluorides, and to a copending application of W. G. Woods et al, Ser. No. 878,262 filed Nov. 19, 1969, which describes and claims the preparation of N-substituted -2,6-dinitro-3-halo-4-trifluoromethylanilines.

The compounds of this invention are excellent herbicides and are especially useful as selective herbicides for controlling weeds in the presence of desirable crops, particularly field beans, peanuts, cotton and soybeans.

The preferred compounds of this invention are especially effective against broad-leaf weeds such as lambsquarters, mustard, teaweed and sesbania (coffee weed), which are difficult to control with the known N-(cycloalkyl)alkyl-2,6-dinitro-4-trifluoromethylaniline herbicides which are unsubstituted at the 3-position.

The compounds can be applied as both a pre-emergence or a post-emergence treatment; that is, they can be applied to soil in which the weeds will grow or they can be used to kill or suppress the growth of weeds or to kill or prevent the emergence of seedlings of undesirable plants. Thus, the compounds can be used to control the growth of weeds by applying a phytotoxic amount of one or more of the active compounds of this invention to the locus to be protected, that is, soil in which the weeds are growing or will grow or the foilage of the growing plants. If desired, the compounds can be incorporated by mixing into the upper 1 to 4 inches of the soil. "Weeds" as used herein is meant to include any plant growth which is undesirable.

Generally, an application rate of from about 0.1 to about 25 pounds of one or more of the active compounds per acre is effective in controlling plant growth. Preferably, the compounds are applied as a pre-emergence treatment at an application rate of from about 0.25 to about 5 pounds per acre. At such rates, the undesirable weeds are killed or stunted with little or no injury to desirable crops.

The following examples illustrate the herbicidal activity of typical compounds of this invention.

EXAMPLE V

The compounds to be tested were evaluated as both pre-emergence and post-emergence treatments on a representative class of weeds and crops. Greenhouse flats were planted to soybeans, velvetleaf, oats, millet and the flats sprayed on the same day as planting with an ethanol solution of the compound to be tested at a rate of five pounds per acre.

Another set of flats with the same plants was treated after the plants had emerged and were about 1 inch in height. These flats were also sprayed with an ethanol solution of the compound at a rate of five pounds per acre in order to determine post-emergence activity. The flats were kept in the greenhouse and watered when needed. Twenty-one days after treatment, the flats were evaluated for herbicidal activity and rated on a 0 to 9 scale in which: 0=no injury, 1=less than 10% injury, 2=10–40% injury, 3=40–70% injury, 4=more than 70% injury, 5=below 25% kill, 6=25–50% kill, 7=50–75% kill, 8=75–99% kill, and 9=100% kill. The following results were obtained.

TABLE I

| | Activity[1] | | | | | | | |
|---|---|---|---|---|---|---|---|---|
| | SO | | VL | | O | | MI | |
| Compound[2] | Pre | Post | Pre | Post | Pre | Post | Pre | Post |
| A | 3 | 4 | 6 | 5 | 5 | 2 | 9 | 5 |
| B | 5 | 4 | 5 | 4 | 1 | 1 | 9 | 5 |

[1]SO = Soybeans; O = Oats; VL = Velvet Leaf; MI = Millet
[2]Compound A = N3-Cyclopropylmethyl-N3-ethyl-2,4-dinitro-6-trifluoromethyl-1,3-phenylenediamine
Compound B = N3-Cyclopropylmethyl-N3-n-propyl-2,4-dinitro-6-trifluoromethyl-1,3-phenylenedimine

EXAMPLE VI

An ethanol solution of the compound being tested was applied to Anaheim, California, sandy loam soil at a rate of 1 pound per acre and then incorporated by mixing in a greenhouse flat. On the same day, corn, rice, soybeans, wheat, barley, cotton, field beans, Jimson weed, wild oats, mustard, teaweed, foxtail, millet, coffee weed, puncture vine, watergrass, pigweed, velvetleaf, and morning glory were planted in the treated soil. The flats were kept in the greenhouse and watered when needed. Twenty-eight days after treatment, the flats were examined and the plants rated for herbicidal activity as described in Example V. The results obtained are shown in Table II.

TABLE II

| | Compound[1] | |
|---|---|---|
| | A | B |
| Corn | 7/4 | 5/3 |
| Rice | 5/4 | 6/4 |
| Soybean | 4 | 2 |
| Wheat | 9 | 9 |
| Barley | 8/4 | 5/4 |
| Cotton | 3 | 2 |
| Field beans | 2 | 2 |
| Jimsonweed | 5/4 | 5/4 |
| Wild oats | 8/4 | 8/3 |
| Mustard | 8/4 | 9 |
| Teaweed | 8/3 | 9 |
| Foxtail | 9 | 9 |
| Millet | 9 | 9 |
| Coffee weed | 7/3 | 9 |
| Puncture vine | 9 | 9 |
| Watergrass | 9 | 9 |
| Pigweed | 9 | 9 |
| Velvetleaf | 5/4 | 7/4 |
| Morning glory | 6/4 | 6/4 |

[1]Compound A = N3-Cyclopropylmethyl-N3-ethyl-2,4-dinitro-6-trifluoromethyl-1,3-phenylenediamine
Compound B = N3-Cyclopropylmethyl-N3-n-propyl-2,4-dinitro-6-trifluoromethyl-1,3-phenylenediamine
Where two numbers, i.e. 8/4, are given as the herbicidal rating, the first number indicates the percent kill and the second number indicates the percent injury to the remaining plants.

EXAMPLE VII

The following experiments were carried out in order to compare the herbicidal activity of two representative compounds of the present invention (Compounds A and C) with corresponding dinitroaniline compounds described by Maravetz in U.S. Pat. No. 3,672,864 (Compounds B and D). The experiments were carried out in flats in the greenhouse. An ethanol solution of each compound to be tested was applied at the indicated rates by spraying the surface of the soil in the flat and then incorporating by mixing the compound into the upper one inch of soil. Each compound was applied at rates of $\theta$, ½ and 1 pound per acre. After treatment of the soil and incorporation, the crop and weed seeds were planted; the smaller seeds were planted at a depth of ½ inch and the larger seeds at a depth of one inch. The flats were planted to the crops peanuts, soybeans, rice, cotton, corn, dry beans, wheat and alfalfa, and the weeds, watergrass, Johnsongrass, foxtail, lambsquarters, teaweed, pigweed, Jimsonweed, wild oats, morning glory, sesbania, velvetleaf, mustard and millet. The flats were kept in the greenhouse and watered when needed. Twenty-one days after treatment, the flats were examined and the plants rated for herbicidal activity based on a comparison with untreated controls using the rating scale of Example V. The results are given in Table III.

TABLE III

| Plant | Compound A (Rate lb/A.) | | | Compound B (Rate lb/A.) | | | Compound C Rate lb/A.) | | | Compound D (Rate lb/A.) | | |
|---|---|---|---|---|---|---|---|---|---|---|---|---|
| | 0.25 | 0.5 | 1.0 | 0.25 | 0.5 | 1.0 | 0.25 | 0.5 | 1.0 | 0.25 | 0.5 | 1.0 |
| Peanuts | 0 | 0 | 1 | 0 | 0 | 2 | 0 | 1 | 1 | 1 | 2 | 2 |
| Soybeans | 1 | 1 | 6 | 1 | 1 | 1 | 1 | 5 | 5 | 1 | 1 | 5 |
| Rice | 7 | 8 | 9 | 5 | 7 | 9 | 2 | 8 | 8 | 7 | 7 | 8 |
| Cotton | 0 | 0 | 1 | 0 | 0 | 2 | 1 | 1 | 0 | 1 | 1 | 2 |
| Corn | 5 | 7 | 8 | 6 | 6 | 7 | 0 | 5 | 5 | 2 | 8 | 6 |
| Drybeans | 0 | 2 | 2 | 1 | 0 | 2 | 0 | 1 | 0 | 0 | 0 | 6 |
| Wheat | 8 | 8 | 8 | 1 | 8 | 8 | 3 | 7 | 9 | 1 | 5 | 6 |
| Watergrass | 9 | 9 | 9 | 9 | 9 | 9 | 9 | 9 | 9 | 8 | 9 | 9 |
| Alfalfa | 8 | 8 | 9 | 7 | 8 | 8 | 7 | 6 | 8 | 5 | 5 | 8 |
| Johnsongrass | 9 | 8 | 9 | 8 | 9 | 9 | 8 | 8 | 9 | | | |
| Foxtail | 9 | 9 | 9 | 8 | 9 | 9 | 9 | 9 | 9 | 7 | 9 | 9 |
| Lambsquarters | 9 | 9 | 9 | 7 | 8 | 9 | 9 | 9 | 9 | 5 | 8 | 9 |
| Teaweed | 7 | 8 | 8 | 1 | 7 | 8 | 7 | 8 | 8 | 2 | 6 | 7 |
| Pigweed | 9 | 9 | 9 | 9 | 9 | 9 | 9 | 9 | 9 | 8 | 9 | 9 |
| Jimsonweed | 5 | 5 | 7 | 1 | 5 | 5 | 2 | 2 | 5 | 2 | 5* | 2 |
| Wild oats | 7 | 6 | 7 | 6 | 8 | 9 | 3 | 7 | 8 | 7 | 8 | 8 |
| Morning glory | 5 | 7 | 7 | 2 | 6* | 3 | 2 | 5 | 5 | 2 | 2 | 2 |
| Sesbania | 5 | 6 | 6 | 2 | 8* | 3 | 5 | 2* | 5 | 1 | 2 | 5 |
| Velvetleaf | 2 | 5 | 6 | 5* | 2 | 3 | 1 | 5* | 3 | 2 | 2 | 2 |
| Mustard | 8 | 9 | 9 | — | 1 | 5 | 1 | 9 | 8 | 6* | 2 | 1 |
| Millet | 8 | 9 | 8 | 7 | 8 | 9 | 5 | 9 | 9 | 7 | 7 | 9 |

*an obvious experimental anomaly
Compound A = N³-Cyclopropylmethyl-N³-ethyl-2,4-dinitro-6-trifluoromethyl-1,3-phenylenediamine
Compound B = N-Cyclopropylmethyl-N-ethyl-2,6-dinitro-4-trifluoromethylaniline
Compound C = N³-Cyclopropylmethyl-N³-n-propyl-2,4-dinitro-6-trifluoromethyl-1,3-phenylenediamine
Compound D = N-Cyclopropylmethyl-N-n-2,6-dinitro-4-trifluoromethylaniline It is apparent from the above results that the phenylenediamines (A and C) are superior herbicides for controlling broadleaf weeds such as lambsquarters, teaweed, sesbania and mustard, especially at the low, economical rates of 0.25 and 0.5 pound per acre.

Since a relatively small amount of one or more active N³-(cycloalkyl)-alkyl-2,4-dinitro-6-trifluoromethyl-1,3-phenylenediamine should be uniformly distributed over the area to be treated, the compounds preferably are formulated with conventional herbicide carriers, either liquid or solid. Thus, the compounds can be impregnated on or a mixed with a pulverulent solid carrier such as lime, talc, clay, bentonite, calcium chloride, vermiculite, calcium carbonate, and the like. Alternatively, the compounds can be dissolved or suspended in a liquid carrier such as water, kerosene, alcohols, diesel oil, xylene, benzene, glycols, ketones, and the like. A surfactant preferably is included to aid in dispersion, emulsification and coverage. The surfactant can be ionic or non-ionic, and may be liquid or a solid. The use of the term "surfactant" herein is intended to include such compounds commonly referred to as wetting agents, dispersing agents and emulsifying agents. Typical surfactants include tha alkylarylsulfonates, the fatty alcohol sulfates, sodium salt of naphthalenesulfonic acid, alkylaryl polyether alcohols, long chain quaternary ammonium compounds, sodium salts of petroleum-derived alkylsulfonic acids, polyoxyethylene-sorbitan monolaurate, and the like. These dispersing and wetting agents are sold under numerous trademarks and may either be pure compounds, mixtures of compounds of the same general group or they can be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with a locally available carrier, preferably water, thereby keeping shipping costs to a minimum while providing a product which can be used with a minimum of equipment and effort. Such concentrates may contain from about 5 to about 99 percent by weight of one or more of the active N³-(cycloalkyl)-alkyl-2,4-dinitro-6-trifluoromethyl-1,3-phenylenediamines with a carrier or diluent, which may be a liquid or a solid. Liquid carriers which are miscible with the active agent or other liquids in which the compound may be suspended or dispersed can be used. A surfactant is also generally included to facilitate such dilution or dispersion in water. However, the surfactant itself may comprise the carrier in such concentrates.

The herbicidal compositions can include other beneficial adjuvants, such as humectants, oils and contact agents. Also, other herbicides such as the sodium borates, sodium chlorate, chlorophenoxyacetic acids, substituted uracils and ureas, triazines, benzimidazoles, carbamates, anilides, amides, and haloalkanoic acids, can be included in the formulation.

Various changes and modifications of the invention can be made, and to the extent that such variations incorporate the spirit of this invention, they are intended to be included within the scope of the appended claims.

What is claimed is:

1. A compound of the formula

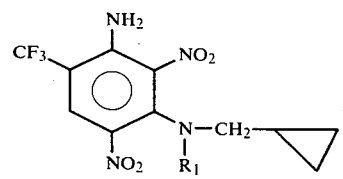

wherein $R_1$ is alkyl of 1 to 4 carbon atoms.

2. A compound according to claim 1 wherein $R_1$ is n-propyl.

3. A compound according to claim 1 wherein $R_1$ is ethyl.

UNITED STATES PATENT OFFICE
CERTIFICATE OF CORRECTION

Patent No. 4,201,724    Dated May 6, 1980

Inventor(s) DON L. HUNTER & WILLIAM G. WOODS

It is certified that error appears in the above-identified patent and that said Letters Patent are hereby corrected as shown below:

In the Abstract, correct the formula to read:

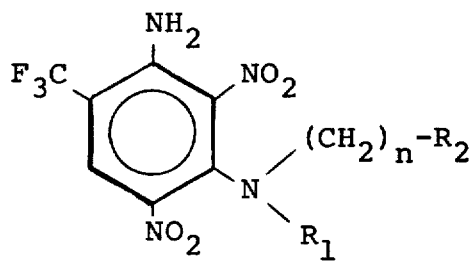

In column 6, line 53, change -- 0, 1/2 -- to "1/4, 1/2".

UNITED STATES PATENT OFFICE
CERTIFICATE OF CORRECTION

Patent No. 4,201,724      Dated May 6, 1980

Inventor(s) DON L. HUNTER & WILLIAM G. WOODS

It is certified that error appears in the above-identified patent and that said Letters Patent are hereby corrected as shown below:

In columns 7 and 8 (TABLE III);

Corn:   Under Compound D (Rate 0.5 lb/A.),
        change -- 8 -- to "8*".

Johnsongrass:   Under Compound C (Rate 0.5 lb/A.),
        change -- 8 -- to "9".

Johnsongrass:   Under Compound D (Rate lb/A.),
        insert "8   8   9".

Pigweed:   Under Compound B (Rate 0.25 lb/A.),
        change -- 9 -- to "8".

Signed and Sealed this

First Day of July 1980

[SEAL]

Attest:

Attesting Officer

SIDNEY A. DIAMOND

Commissioner of Patents and Trademarks